United States Patent
Ellingboe et al.

(10) Patent No.: US 9,969,127 B2
(45) Date of Patent: May 15, 2018

(54) CONVERTIBLE BLANKET

(71) Applicant: SMITHS MEDICAL ASD, INC., Rockland, MA (US)

(72) Inventors: Jay Ellingboe, New Brighton, MN (US); Kristin Finberg, Minneapolis, MN (US); Alan Stec, Bridgewater, MA (US); Bryan Stoddard, Minneapolis, MN (US); Chris Zander, Hudson, WI (US)

(73) Assignee: Smiths Medical ASD, Inc., Plymouth, MN (US)

( * ) Notice: Subject to any disclaimer, the term of this patent is extended or adjusted under 35 U.S.C. 154(b) by 848 days.

(21) Appl. No.: 14/186,034

(22) Filed: Feb. 21, 2014

(65) Prior Publication Data

US 2014/0257442 A1    Sep. 11, 2014

Related U.S. Application Data

(60) Provisional application No. 61/772,799, filed on Mar. 5, 2013.

(51) Int. Cl.
  *B29C 65/00*   (2006.01)
  *A61F 7/00*    (2006.01)

(52) U.S. Cl.
  CPC .......... *B29C 66/439* (2013.01); *A61F 7/0097* (2013.01); *A61F 2007/006* (2013.01);
  (Continued)

(58) Field of Classification Search
  None
  See application file for complete search history.

(56) References Cited

U.S. PATENT DOCUMENTS 5,072,455 A    12/1991  St Ours
5,443,488 A *   8/1995  Namenye .............. A61F 7/0097
                                                                165/46
(Continued)

FOREIGN PATENT DOCUMENTS

CN           102405006 A     4/2012
WO      WO 2004-047884       6/2004
(Continued)

OTHER PUBLICATIONS

PCT Search Report and Written Opinion of the ISA/KR, dated Jun. 3, 2014 re: PCT/US214/017645.
(Continued)

*Primary Examiner* — Joseph Stoklosa
*Assistant Examiner* — Adam Avigan
(74) *Attorney, Agent, or Firm* — Louis Woo

(57) ABSTRACT

A convective blanket may be converted from an underbody blanket to a combination over body and underbody blanket by having an openable seal positioned substantially orthogonal to the longitudinal axis of the blanket away from the head area of the blanket. The seal may be preformed with a line of weakness so that it may readily be separated to form an opening for the head of the patient. The upper portion and the main portion of the blanket may be folded relatively towards each other to cover opposite sides of the patient. Elongate openings are provided in the main portion of the blanket to allow the arms of the patient to extend through the blanket.

14 Claims, 5 Drawing Sheets

(52) U.S. Cl.
CPC ............ *A61F 2007/0091* (2013.01); *A61F 2007/0098* (2013.01); *Y10T 156/1057* (2015.01)

(56) References Cited

U.S. PATENT DOCUMENTS

| | | | |
|---|---|---|---|
| 5,694,963 A | 12/1997 | Fredell | |
| 5,735,890 A | 4/1998 | Kappel et al. | |
| 5,773,275 A | 6/1998 | Anderson et al. | |
| 5,839,133 A | 11/1998 | Dickerhoff et al. | |
| 6,994,720 B2 | 2/2006 | Gammons | |
| 7,666,214 B2 | 2/2010 | Pierre et al. | |
| 7,716,940 B2 | 5/2010 | Farnworth et al. | |
| 7,762,096 B2 | 7/2010 | Fuchs | |
| 8,172,890 B2 | 5/2012 | Pierre et al. | |
| 2003/0195596 A1 | 10/2003 | Augustine | |
| 2004/0011073 A1 | 1/2004 | Blackstone | |
| 2005/0125047 A1 | 6/2005 | Gammons | |
| 2006/0052851 A1* | 3/2006 | Anderson | A61F 7/0097 607/104 |
| 2007/0068651 A1* | 3/2007 | Gammons | A61F 7/02 165/46 |
| 2007/0244532 A1 | 10/2007 | Pierre et al. | |
| 2007/0244533 A1* | 10/2007 | Pierre | A61F 7/02 607/107 |
| 2008/0027522 A1 | 1/2008 | Bieberich | |
| 2009/0248120 A1* | 10/2009 | Starr | A61F 7/00 607/107 |
| 2010/0211139 A1* | 8/2010 | Pierre | A61F 7/0097 607/104 |
| 2011/0009930 A1 | 1/2011 | Officier et al. | |

FOREIGN PATENT DOCUMENTS

| | | |
|---|---|---|
| WO | WO 2004/047884 A2 | 6/2004 |
| WO | WO 2011-087484 | 7/2011 |
| WO | WO 2011/087484 A2 | 7/2011 |

OTHER PUBLICATIONS

EP Search Report issued in corresponding EP Application No. EP 14 76 0519, dated Sep. 29, 2016.

Chinese office action issued in corresponding CN Application No. 201480012420.X, dated Aug. 3, 2016.

* cited by examiner

CONVERTIBLE BLANKET

FIELD OF THE INVENTION

The present invention relates to convective warming blankets and more particularly to an underbody blanket that can be converted into a poncho like combination over body and underbody blanket for use by a patient in a repose position, or standing and sitting positions.

BACKGROUND OF THE INVENTION

In U.S. Pat. No. 8,172,890, assigned to the same assignee as the instant application, there is disclosed a combination underbody and over body blanket configured as a full body blanket in support of a patient. The '890 blanket has an opening at the mid portion of the blanket for passage of the head of the patient when the upper portion of the blanket is folded back onto the patient. The opening for the '890 blanket is pre-configured into the blanket. The disclosure of the '890 patent is incorporated by reference herein.

SUMMARY OF THE PRESENT INVENTION

The convective blanket of the instant invention is an underbody blanket that is convertible to a poncho type blanket, as there is no predefined opening that allows the head of the patient to extend through the blanket. More particularly, the blanket of the instant invention is an inflatable structure that may be divided into an upper (or minor) portion and a main (or major) portion. There is a non-inflatable body area at the main body portion. A non-inflatable head area is also provided substantially in the main portion of the blanket. Thus, when a patient is positioned onto the upper sheet of the convective blanket, his head would rest on the non-inflatable head area while his body rests on the non-inflatable body area. The length of the blanket is such that the bottom end of the blanket, depending on the size of the patient, is supportive of the buttocks of the patient. Two air inlet ports are provided to the blanket, one at each longitudinal edge of the blanket, to enable the input of a fluid such as air to inflate the blanket.

A semicircular or curvilinear seal is provided in the upper portion of the blanket away from the non-inflatable head area. The seal has substantially along its length a line of weakness or perforations that allows the seal to be readily opened, so that the upper portion of the blanket and the main portion of the blanket may be folded relatively towards each other, with the thus torn seal providing an opening to expose the head of the patient or through which the head of the patient may pass. When thus converted from an underbody blanket to a combination upper body and lower body blanket, the blanket of the instant invention becomes a poncho blanket where opposite sides of the patient, for example the front and the back of the patient, are covered by the upper and main portions, respectively, of the blanket.

There are two elongate openings, each defined by a corresponding non-ending seal, that extend longitudinally along substantially the length of the main portion of the blanket. These elongate openings sandwich the non-inflatable body area and possibly a portion of the non-inflatable head area. The elongate openings allow the arms of the patient to extend therethrough so that the patient may be wrapped longitudinally by the opposite outer side portions of the blanket. When the blanket is used as a poncho blanket, with the upper portion in contact with the front of the patient and the main portion in contact with the back of the patient, the upper body of the patient is substantially enveloped by the blanket in a semi-cocoon like state, with only the top portion of the head or the face of the patient exposed. As apertures are provided in the upper sheet of the blanket that comes into contact with the patient, the patient not only is being warmed by conduction by being in contact with the heated upper sheet of the blanket, but he is also warmed by an envelope of heated air output from the apertures in the upper sheet of the blanket.

Given that the blanket of the instant invention is not a full body blanket, it can readily be used to warm the patient while the patient is seated, or is standing, provided that the air hose for inputting heated air into the blanket via either one of the inlet ports provided along the respective longitudinal edges of the blanket is of sufficient length. The blanket may moreover be used in a number of different ways to provide coverage for different parts of the patient.

The present invention is therefore directed to a convective blanket adapted to cover the front and back of a user that comprises: an air impermeable upper sheet and an air impermeable lower sheet bonded to each other at their respective peripheries to form an inflatable structure having a minor portion and a major portion foldable relative to each other along a longitudinal axis; a body area at the major portion whereto the back of the user contacts and a head area whereto the head of the user contacts when the user is positioned relative to the upper sheet of the blanket with his back facing the major portion, each of the body and head areas defined by a pair of longitudinal sides; a plurality of apertures in the upper sheet to output air in the structure to the user; and a longitudinal seal in substantial orthogonal relationship to the longitudinal axis of the blanket located at the minor portion away from the head area, the seal having a length with respective ends extending beyond the longitudinal sides of the head area, the seal being openable to expose the head of the user or to enable the head of the user to pass through when the minor portion and the major portion are folded relatively towards each other so that the minor portion covers the front of the user while the major portion covers the back of the user.

The instant invention is also directed to a convective blanket adapted to cover opposite sides of a user, comprising: an air impermeable upper sheet and an air impermeable lower sheet bonded to each other at their respective peripheries to form an inflatable structure having a minor portion and a major portion along a longitudinal axis; two elongate openings each defined by a non-ending seal extending longitudinally along substantially the length of the major portion, the elongate openings sandwiching a body area adapted to be in contact with the user when the user is positioned relative to the upper sheet of the blanket; a seal at the minor portion located away from a head area at the structure adapted to come into contact with the head of the user, the seal having a length that extends substantially orthogonal to the longitudinal axis of the structure, the seal being openable to expose the head of the user or to enable the head of the user to pass through when the minor portion and the major portion are folded relatively towards each other so that the minor portion comes into contact with one of the opposite sides of the user while the body portion comes into contact with other of the opposite sides of the user.

The instant invention is moreover directed to a method of manufacturing a convective blanket adapted to cover opposite sides of a user, comprising the steps of:

(a) bonding an air impermeable upper sheet and an air impermeable lower sheet to each other at their respective peripheries to form an inflatable structure having an minor portion and a major portion along a longitudinal axis, the minor and major portions foldable relatively toward each other;

(b) providing a body area at the major portion whereto at least one side of the user comes into contact with and a head area whereto the head of the user comes into contact with when the user is positioned relative to the upper sheet of the blanket, each of the body and head areas defined by a pair of longitudinal sides;

(c) providing a plurality of apertures in the upper sheet to output air in the structure to the user; and (d) locating a longitudinal seal in substantial orthogonal relationship to the longitudinal axis of the blanket at the minor portion away from the head area, the seal having a length with respective ends extending beyond the longitudinal sides of the head area, the seal being openable to expose the head of the user or to enable the head of the user to pass through when the minor portion and the major portions are folded relatively towards each other so that the minor portion is in contact with one of the opposites sides of the user while the major portion is in contact with other of the opposite sides of the user.

BRIEF DESCRIPTION OF THE FIGURES

The present invention will become apparent and the invention itself will be best understood with reference to the following description of the invention taken in conjunction with the following drawings, wherein.

DETAILED DESCRIPTION OF THE INVENTION

Figure 1:
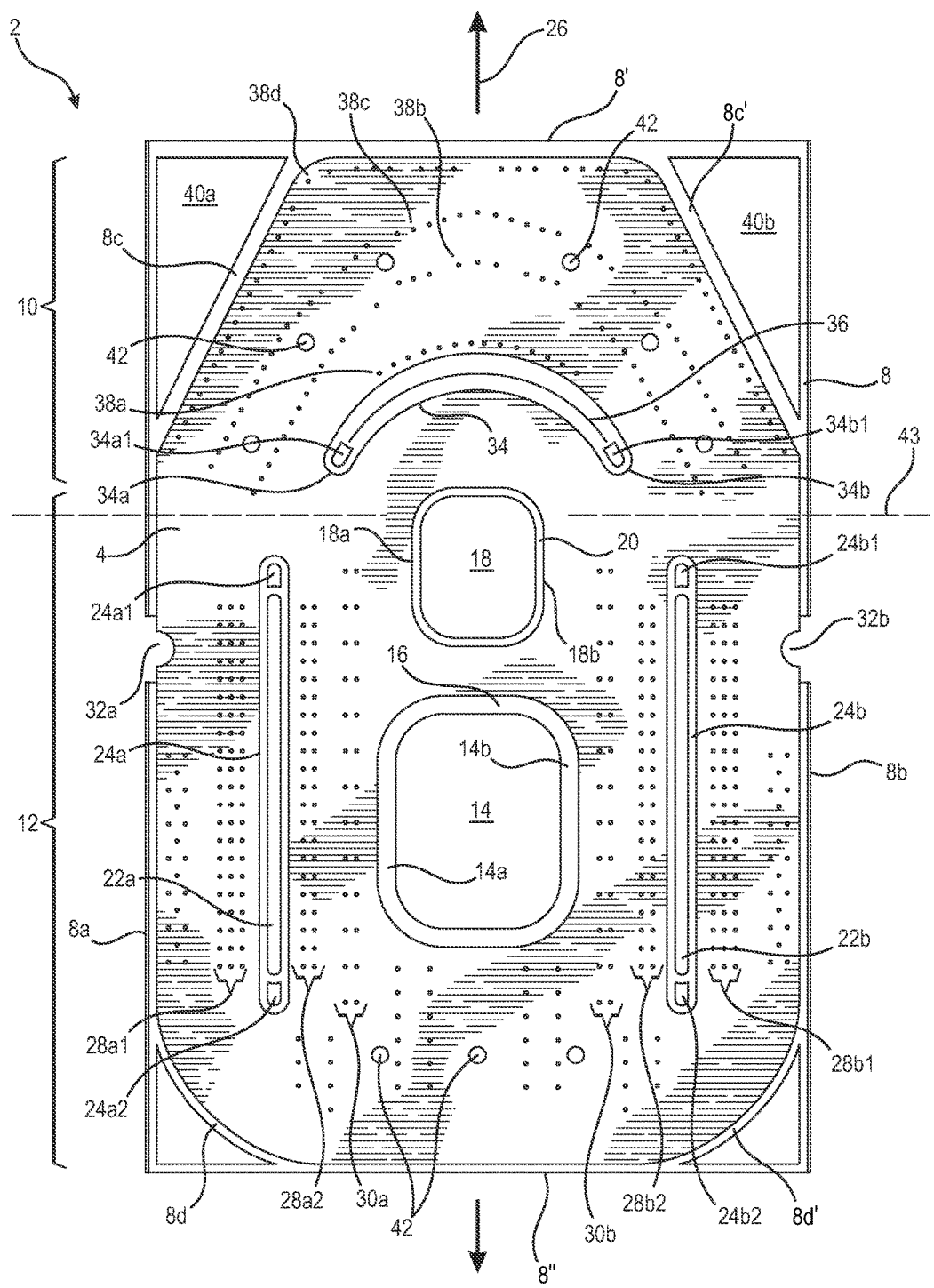
FIG. 1 is a plan view of the blanket of the instant invention.

With reference to FIG. 1, the inventive blanket 2 of the instant invention is shown to have an upper sheet 4 and a lower sheet 6 (shown in FIG. 2 where the underside of the blanket is folded over) bonded at their respective peripheries 8 to form an inflatable convective blanket structure. For discussion purpose, the inflatable structure is shown to have an upper, or minor portion 10, and a main, or major portion 12. It should be noted that the portions 10 and 12 shown in FIG. 1 are for illustration purpose, and therefore they do not represent precisely the demarcation of the upper and main portions of the blanket.

At main portion 12, there is an uninflated body area 14 with two longitudinal sides 14a and 14b defined by a non-ending seal 16. A non-inflatable head area 18 with two longitudinal sides 18a and 18b, defined by a non-ending seal 20, is also provided on the blanket. Head area 18 is shown in the exemplar blanket of FIG. 1 to be either completely within main portion 12 or straddling upper portion 10 and main portion 12.

There are two elongate openings 22a and 22b provided longitudinally along substantially the length of main portion 12. The elongate openings 22a and 22b sandwich therebetween body area 14 and, as shown, a portion of head area 18.

The elongate openings 22a and 22b are defined by non-ending seals 24a and 24b, respectively, in the exemplar blanket of FIG. 1. There are at the respective ends of the elongate openings 22a and 22b strain relief sealed air pockets 24a1 and 24a2 for non-ending seal 24a, and sealed air pockets 24b1 and 24b2 for non-ending seal 24b.

Multiple arrays or sets of rows of apertures are provided along the length of the blanket in parallel alignment with the blanket's longitudinal axis 26. In particular, there are two arrays of apertures extending longitudinally along each longitudinal side of each of the elongate openings 22a and 22b. These arrays of apertures are designated 28a1 and 28a2 for elongate opening 22a, and 28b1 and 28b2 for elongate opening 22b. There in turn are three rows of apertures for arrays 28a1 and 28b1, and two rows of apertures for arrays 28a2 and 28b2. In addition, two arrays of two rows of apertures 30a and 30b extend longitudinally along the respective longitudinal sides of body area 14 and a portion of head area 18. Additional apertures are provided in the upper sheet at the main portion of the blanket for outputting heated air circulating within the inflated structure.

For the exemplar blanket of FIG. 1, two air inlet ports 32a and 32b are provided along the respective longitudinal edges of the blanket. As shown, inlet port 32a is provided at longitudinal edge 8a of the blanket while inlet port 32b is provided at longitudinal edge 8b of the blanket. It should be noted that the positioning of inlet ports 32a and 32b are for illustration only, as those inlet ports may in practice be positioned further up or down along the respective longitudinal edges 8a and 8b of the blanket. It should further be noted that only one of the inlet ports is used for inputting heated air to inflate the blanket. The inlet ports are constructed in accordance to the disclosure in U.S. Pat. No. 7,658,756, also assigned to the assignee of the instant application. The disclosure of the '756 patent is incorporated by reference herein.

There is provided at the upper or minor portion 10 of the blanket a semicircular or curvilinear seal 34. Seal 34 is positioned away from head area 18 and is configured curvilineally such that its respective ends 34a and 34b extend beyond the two longitudinal sides of head area 18, designated as part of the non-ending seal 20 by reference numbers 18a and 18b. There is provided along substantially the entire length of seal 34 a line of weakness or perforations 36 that enables a user to readily tear along line 36 to thus separate seal 34 to effect an opening. Strain relief air pockets 34a1 and 34b1 are provided at the respective ends 34a and 34b of seal 34 act as a safeguard to prevent the tearing of seal 34 beyond its respective ends 34a and 34b.

One row of apertures 38a circumscribes the top of seal 34. Three other rows of apertures 38b, 38c and 38d in curvilinear spatial alignment relationship with seal 34 are provided in upper sheet 4 of the blanket in upper portion 10. As shown, upper portion 10 of the exemplar blanket 2, as defined by peripheral seals 8c and 8c' from head end 8', has a shape in the form of an isosceles trapezoid. For main portion 12, at the bottom end 8" of the blanket, seal sections 8d and 8d' of peripheral seal 8 round the lower corners of the blanket. The configuration of the exemplar blanket as shown in FIG. 1 is found to facilitate or enhance the circulation of the air flowing within the inflated blanket structure.

Figure 2:
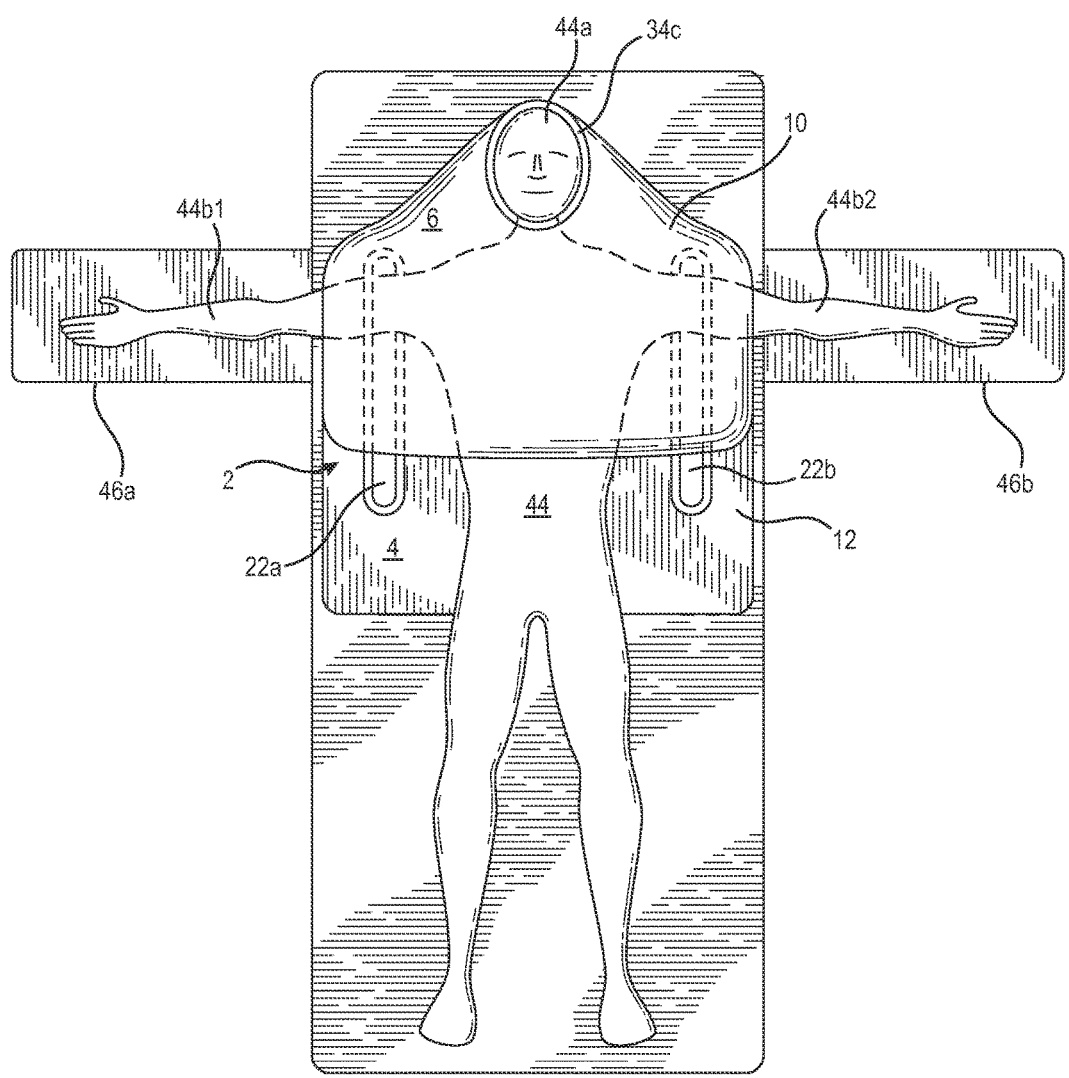
FIG. 2 shows the blanket being used on a patient in a repose position.

The sealed non-inflatable corner portions 40a and 40b at upper portion 10 may each be provided with an adhesive mechanism, for example a tape, to secure upper sheet 4 of upper portion 10 of the blanket to the body of the patient when upper portion 10 is folded over, per shown in FIG. 2.

A number of bonded spots 42 are provided strategically throughout blanket 2 to prevent the inflated structure from ballooning.

The exemplar blanket shown in FIG. 1 may be used as an underbody blanket whereby the patient is placed onto the blanket, with the head of the patient resting on non-inflatable head area 18 and the torso of the patient resting on the body area 14.

The exemplar blanket of FIG. 1 may be converted into a combination underbody and over body blanket, per shown in FIG. 2. There, seal 34 has been separated along the line of perforations 36 to effect an opening 34*c*, to expose the head of the patient or through which the head of the patient may extend, when upper portion 10 of the blanket is folded back, for example along illustrative dotted line 43, towards main portion 12. As shown, upper sheet 4 of the blanket, for both upper portion 10 and main portion 12, is in contact with the patient or user 44. The head 44*a* of the patient is shown to be exposed through opening 34*c*. As further shown in FIG. 2, the back of the body of patient 44 is covered by, or in contact with, main portion 12 and the front of the patient is covered by, or in contact with, upper portion 10 of the blanket. Arms 44*b*1 and 44*b*2 of the patient are shown to extend through elongate openings 22*a* and 22*b*, respectively, and rest on corresponding arm supports 46*a* and 46*b*.

Figure 3:
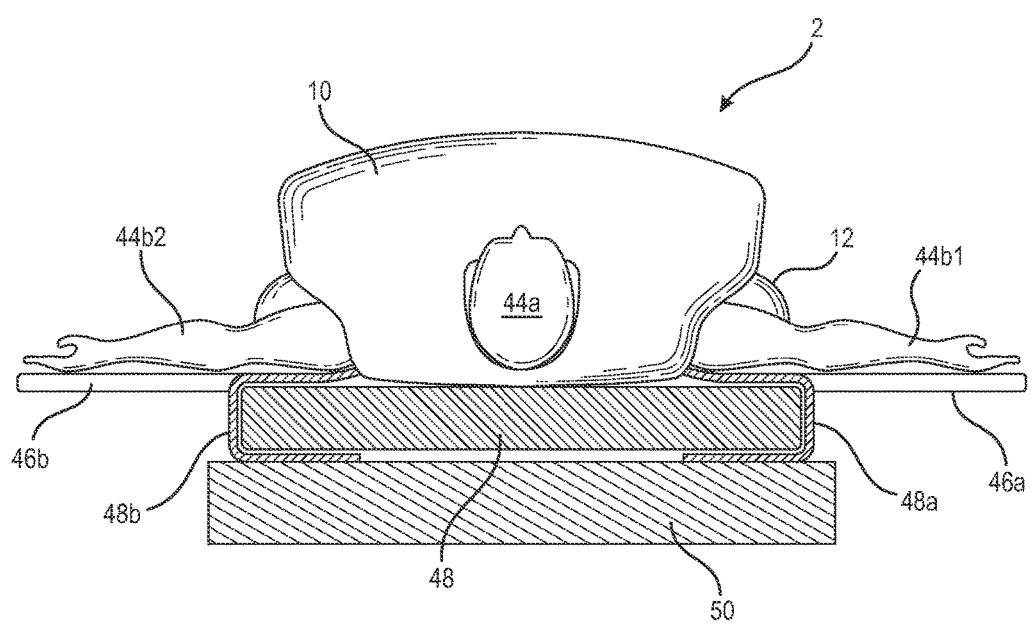
FIG. 3 is a end view of the patient lying on the blanket.

With reference to FIGS. 2 and 3, it can be seen that the blanket, or rather main portion 12 of the blanket, is positioned onto a bed or mattress 48, which in turn is placed on a table support 50. In FIG. 3, arms 44*b*1 and 44*b*2 of the patient are shown to extend away from blanket 2 so that, aside from the head 44*a* and the arms of the patient, the upper body of the patient is substantially covered by blanket 2. From the end view of FIG. 3, blanket 2 is shown to have two optional tuck flaps 48*a* and 48*b*, attached to the underside of the blanket, that may be used to secure the blanket onto mattress 48, by having the lower part of the tuck flaps tucked between mattress 48 and bed support 50. The optional tuck flaps 48*a* and 48*b* are further shown, in both solid and dotted lines, in the alternative exemplar embodiment of the blanket in FIG. 5.

Figure 4A:
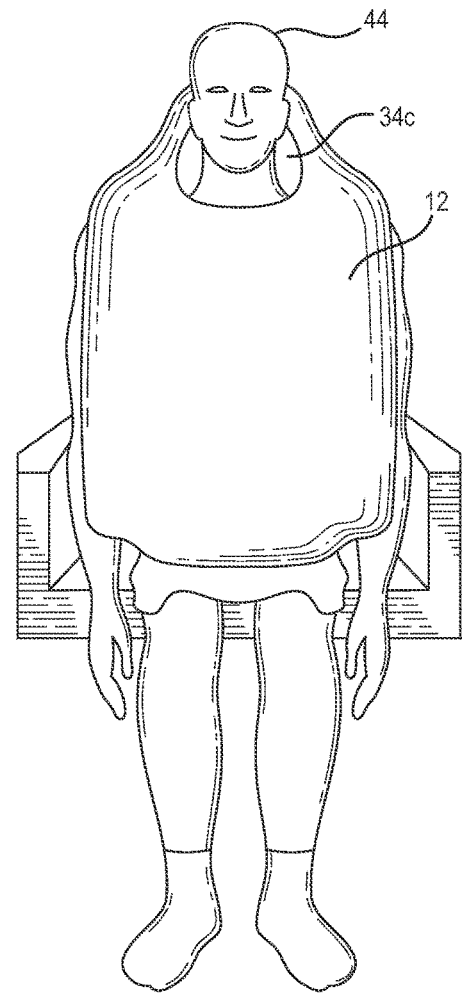
FIGS. 4A and 4B show the front and side views, respectively, of a patient using the blanket of the instant invention in a different way.
Figure 4B:
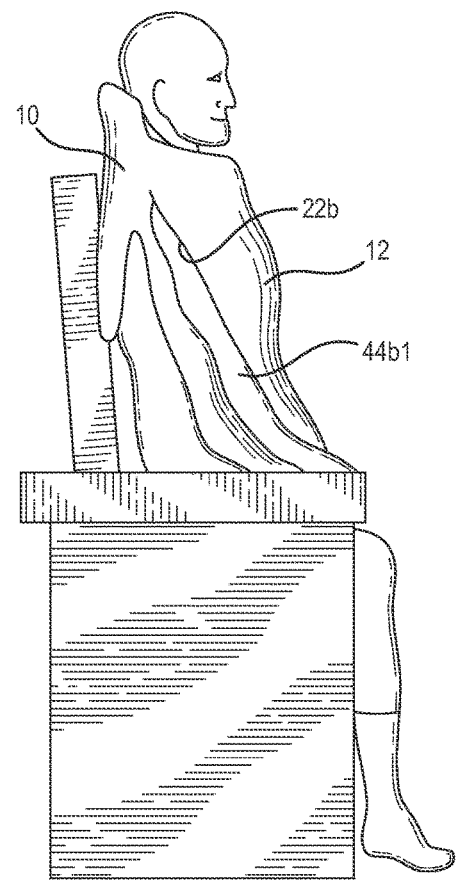

FIGS. 4*a* and 4*b* illustrate another example whereby the blanket of the instant invention covers opposite sides of a user in a non-lying position. Specifically, patient 44 is shown to be in a sitting position with his head extending through opening 34*c* while main portion 12 of the blanket covers his front and upper portion 10 of the blanket covers his back. As shown in FIG. 4*b*, arm 44*b*1 of the patient extends out from the blanket via one of the elongate openings, in this instance elongate opening 22*b*. The opening 34*c* shown in FIG. 4*a* has a larger dimension than the opening shown in the earlier drawings to accommodate the passage of the head of the patient through the opening. It should be appreciated that the inventive blanket may similarly cover opposite sides of a standing patient.

Figure 5:
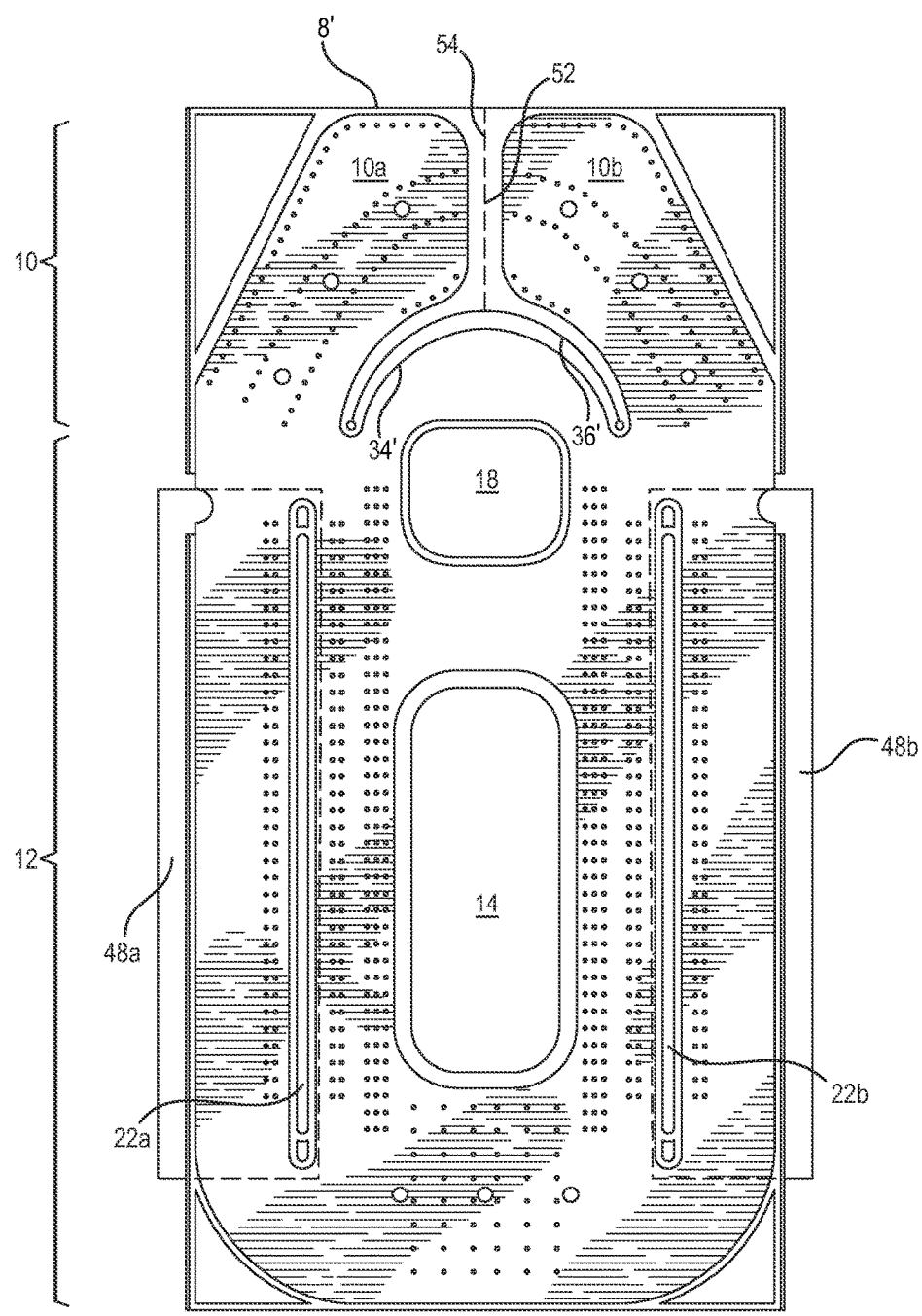
FIG. 5 is an alternate full body embodiment of the inventive blanket.

FIG. 5 shows an alternate embodiment of the inventive blanket. The components for the blanket of FIG. 5 that are the same or function the same as the blanket shown in FIG. 1 are labeled the same. For the FIG. 5 blanket, main portion 12 is longer than that of the FIG. 1 blanket, so that the FIG. 5 blanket may be a full size blanket that is adapted to support the legs of the patient. In addition to the length of main portion 12 being longer than that of the FIG. 1 blanket, the body area 14 for the FIG. 5 blanket has a longer length than the body area of the FIG. 1 blanket. Also, the width of the blanket of FIG. 5 may be narrower than the width of the blanket shown in FIG. 1. The FIG. 5 blanket further differs from the FIG. 1 blanket in that some of the apertures in the FIG. 1 blanket are missing from the exemplar FIG. 5 blanket, the placement of the various apertures between the two blankets are different, and the number of rows of apertures for the different aperture arrays that extend along the longitudinal sides of the elongate openings 22*a* and 22*b* are different between the two exemplar blankets.

Aside from being a full body blanket as compared to the FIG. 1 half body blanket, the FIG. 5 exemplar blanket has a bonded strip 52 that extends from the top end 8' of the blanket to integrally merge with seal 34'. Bonded strip 52 provides a sealed center for upper portion 10 to cover the front of the patient. Advantageously, strip 52 may be cut by a clinician along its length so that the upper portion 10 may be separated into two half upper portions 10*a* and 10*b* to expose the upper torso of the patient. Alternatively, a line of perforations or weakness, designated by dotted line 54, may be preformed on strip 52 to enable upper portion 10 to be readily separated into the two half upper portions 10*a* and 10*b*.

The invention disclosed above is subject to many variations, modifications and changes in detail. For example, instead of covering the patient per shown in FIGS. 2 and 4A-4B, the inventive blanket may also be positioned to align along one side of the body of the patient, when either the right or left side of the patient requires warming or when the patient is lying sideways on the operating table. The major portion of the blanket may be placed over the side of the patient that requires more warming, with the head of the patient acting as the reference point for positioning the upper and main portions of the blanket, since the head of the patient presumably is extending through the opening effected at the junction of the upper and lower portions. Thus, it is intended that all matters described throughout this specification and shown in the accompanying drawings be interpreted as illustrative only and not in a limiting sense. Accordingly, it is intended that the invention be limited only by the spirit and scope of the hereto appended claims.

The invention claimed is:

1. A convective blanket adapted to cover the front and back of a user, comprising:
    an air impermeable upper sheet and an air impermeable lower sheet bonded to each other at their respective peripheries to form an inflatable structure having a minor portion and a major portion foldable relative to each other along a longitudinal axis;
    a non-inflatable body area provided at the major portion configured to contact the back of the user and a non-inflatable head area provided at the structure configured to contact the head of the user when the user is positioned relative to the upper sheet of the blanket with his back facing the major portion, each of the body and head areas defined by a pair of longitudinal sides;
    a plurality of apertures in the upper sheet to output air in the structure to the user; and
    a semicircular seal in substantial orthogonal relationship to the longitudinal axis of the blanket located at the minor portion away from the head area, the seal having a length with respective ends extending beyond the longitudinal sides of the head area, the seal being openable to expose the head of the patient or enable the head of the user to pass through when the minor portion and the major portion are relatively folded towards each other so that the minor portion covers the front of the user while the major portion covers the back of the user.

2. Blanket of claim 1, further comprising two elongate openings each defined by a non-ending seal extending longitudinally along substantially the length of the major portion, strain relief means provided at each longitudinal end of each of said non-ending seals, the elongate openings sandwiching at least the body area at the major portion.

3. Blanket of claim 2, further comprising respective arrays of multiple rows of apertures in the upper sheet extending in parallel substantially along each longitudinal side of each of the elongate openings.

4. Blanket of claim 1, wherein a line of perforations or weakness extends along a substantial portion of the length of the seal to enable the seal to be readily opened.

5. Blanket of claim 4, further comprising multiple rows of apertures in the upper sheet in spatial alignment with the semicircular seal.

6. Blanket of claim 1, further comprising at least one inlet port provided along a longitudinal side of the blanket usable to input air into the structure.

7. Blanket of claim 1, wherein the structure is defined longitudinally between a top end and a bottom end, the blanket further comprising a bonded strip extending from the seal to the top end of the structure.

8. Blanket of claim 1, wherein the major portion of the structure at the bottom end has rounded corners and the minor portion of the structure has an isosceles trapezoidal shape to enhance the circulation of air flow in the structure.

9. A convective blanket adapted to cover opposite sides of a user, comprising:
   an air impermeable upper sheet and an air impermeable lower sheet bonded to each other at their respective peripheries to form an inflatable structure having a minor portion and a major portion along a longitudinal axis;
   two elongate openings each defined by a non-ending seal extending longitudinally along substantially the length of the major portion, the elongate openings sandwiching a non-inflatable body area adapted to be in contact with the user when the user is positioned relative to the upper sheet of the blanket;
   a semicircular seal at the minor portion located away from a non-inflatable head area at the structure adapted to come into contact with the head of the user, the seal having a length that extends substantially orthogonal to the longitudinal axis of the structure, the seal being openable to expose the head of the patient or to enable the head of the user to pass through when the minor portion and the major portion are folded relatively towards each other so that the minor portion comes into contact with one of the opposite sides of the user while the body portion comes into contact with other of the opposite sides of the user.

10. Blanket of claim 9, wherein the seal has a line of perforations or weakness along a substantial part of its length so as to be tearable therealong to effect an opening for the head of the user to pass through; and
   wherein each of the non-ending seals has strain relief means at each of its longitudinal ends.

11. Blanket of claim 9, further comprising:
   apertures formed in the upper sheet to enable heated air in the structure to escape, respective rows of apertures provided proximately along each longitudinal side of the body area.

12. Blanket of claim 9, further comprising two inlet ports each positioned along a corresponding longitudinal side of the blanket, each of the inlet ports usable to input air to the structure.

13. Blanket of claim 9, further comprising a bonded strip extending from the seal to a top end of the structure along the longitudinal axis, the bonded strip adapted to be separated along its length to partition the minor portion into two halves to expose the front of the user.

14. Blanket of claim 9, wherein the major portion of the structure has a bottom end with rounded corners and the minor portion of the structure has an isosceles trapezoidal shape to facilitate the circulation of air flow within the inflated structure.

* * * * *